United States Patent
Lee et al.

(10) Patent No.: US 8,801,694 B2
(45) Date of Patent: Aug. 12, 2014

(54) INTRAVESICAL DRUG DELIVERY DEVICE

(75) Inventors: Heejin Lee, Arlington, MA (US); Karen Daniel, Newtonville, MA (US); Hong Linh Ho Duc, Cambridge, MA (US); Michael J. Cima, Winchester, MA (US); Mario Castillo, Coto Laurel, PR (US); Steven Froelich, Conneaut, OH (US); Jordan Dimitrakov, Boston, MA (US); Grace Y. Kim, Cambridge, MA (US)

(73) Assignees: Massachusetts Institute of Technology, Cambridge, MA (US); Children's Medical Center Corporation, Boston, MA (US)

( * ) Notice: Subject to any disclaimer, the term of this patent is extended or adjusted under 35 U.S.C. 154(b) by 1796 days.

(21) Appl. No.: 11/463,956

(22) Filed: Aug. 11, 2006

(65) Prior Publication Data

US 2007/0202151 A1 Aug. 30, 2007

Related U.S. Application Data

(60) Provisional application No. 60/707,676, filed on Aug. 11, 2005, provisional application No. 60/726,490, filed on Oct. 12, 2005.

(51) Int. Cl.
*A61F 2/00* (2006.01)
*A61M 31/00* (2006.01)
*A61L 29/16* (2006.01)
*A61K 9/00* (2006.01)
*A61L 29/06* (2006.01)

(52) U.S. Cl.
CPC .............. *A61K 9/0034* (2013.01); *A61L 29/16* (2013.01); *A61L 2300/63* (2013.01); *A61L 2300/402* (2013.01); *A61L 2300/406* (2013.01); *A61M 31/002* (2013.01); *A61L 2300/45* (2013.01); *A61L 29/06* (2013.01)
USPC ............. 604/517; 604/48; 604/500; 424/422; 424/423; 424/425

(58) Field of Classification Search
None
See application file for complete search history.

(56) References Cited

U.S. PATENT DOCUMENTS 3,854,480 A  12/1974  Zaffaroni
(Continued)

FOREIGN PATENT DOCUMENTS

DE  3332156 A1  3/1985
EP  0 572 932  *  9/2000
(Continued)

OTHER PUBLICATIONS

Lidocaine. Drugs.com, Oct. 2008.*
(Continued)

*Primary Examiner* — Isis Ghali
(74) *Attorney, Agent, or Firm* — Sutherland Asbill & Brennan LLP

(57) ABSTRACT

Implant devices for intravesical administration and local drug delivery. The device has a body which includes a hollow tube formed of a biocompatible material; at least one reservoir in the tube which contains a drug; and one or more apertures through which the drug can be released. The device is configured for minimally invasive insertion into a body cavity, such as the bladder. The hollow tube may be elastomeric to permit the device to be elastically deformed from its initial shape into an elongated shape for passage through a catheter, where following such passage the device can return to or toward its initial shape to facilitate retention of the device in the body cavity. The body may have a narrow, elongated shape effective to permit insertion of the drug delivery device through a catheter without necessarily deforming the body, yet include flexible projections which effect retention within the body cavity.

29 Claims, 10 Drawing Sheets

(56) References Cited

U.S. PATENT DOCUMENTS

| | | | |
|---|---|---|---|
| 3,888,975 A * | 6/1975 | Ramwell | 424/432 |
| 3,901,232 A | 8/1975 | Michaels et al. | |
| 3,935,860 A * | 2/1976 | Hoff | 128/839 |
| 4,016,251 A * | 4/1977 | Higuchi et al. | 424/432 |
| 4,235,236 A | 11/1980 | Theeuwes | |
| 4,392,848 A | 7/1983 | Lucas et al. | |
| 4,449,980 A | 5/1984 | Millar et al. | |
| 4,475,916 A | 10/1984 | Himmelstein | |
| 4,629,449 A | 12/1986 | Wong | |
| 4,655,219 A | 4/1987 | Petruzzi | |
| 4,678,463 A | 7/1987 | Millar | |
| 4,871,542 A | 10/1989 | Vilhardt | |
| 4,968,507 A | 11/1990 | Zentner et al. | |
| 5,366,738 A * | 11/1994 | Rork et al. | 424/473 |
| 5,441,550 A | 8/1995 | Hassenboehler, Jr. et al. | |
| 5,499,997 A | 3/1996 | Sharpe et al. | |
| 5,516,522 A * | 5/1996 | Peyman et al. | 424/426 |
| 5,551,954 A | 9/1996 | Buscemi et al. | |
| 5,709,874 A | 1/1998 | Hanson et al. | |
| 5,788,980 A | 8/1998 | Nabahi | |
| 5,795,591 A * | 8/1998 | Lee et al. | 424/473 |
| 5,797,898 A | 8/1998 | Santini et al. | |
| 5,830,230 A | 11/1998 | Berryman et al. | |
| 5,851,217 A | 12/1998 | Wolff et al. | |
| 5,855,906 A | 1/1999 | McClay | |
| 5,869,081 A | 2/1999 | Jackanicz et al. | |
| 5,972,372 A | 10/1999 | Saleh et al. | |
| 5,989,581 A | 11/1999 | Groenewegen | |
| 6,039,967 A * | 3/2000 | Ottoboni et al. | 424/426 |
| 6,039,968 A | 3/2000 | Nabahi | |
| 6,083,933 A | 7/2000 | Hahn | |
| 6,086,909 A | 7/2000 | Harrison et al. | |
| 6,139,535 A | 10/2000 | Greelis et al. | |
| 6,171,298 B1 * | 1/2001 | Matsuura et al. | 604/891.1 |
| 6,183,461 B1 | 2/2001 | Matsuura et al. | |
| 6,207,180 B1 | 3/2001 | Ottoboni et al. | |
| 6,293,923 B1 | 9/2001 | Yachia et al. | |
| 6,398,718 B1 | 6/2002 | Yachia et al. | |
| 6,416,780 B1 | 7/2002 | Passmore et al. | |
| 6,444,224 B1 | 9/2002 | Rathbone et al. | |
| 6,464,999 B1 | 10/2002 | Huo et al. | |
| 6,482,837 B1 | 11/2002 | Wood | |
| 6,491,666 B1 | 12/2002 | Santini et al. | |
| 6,682,473 B1 | 1/2004 | Matsuura et al. | |
| 6,712,784 B2 * | 3/2004 | Huang | 604/60 |
| 6,730,072 B2 | 5/2004 | Shawgo et al. | |
| 6,746,421 B2 | 6/2004 | Yachia et al. | |
| 6,749,617 B1 | 6/2004 | Palasis et al. | |
| 6,753,011 B2 | 6/2004 | Faour | |
| 6,808,522 B2 | 10/2004 | Richards et al. | |
| 6,875,208 B2 | 4/2005 | Santini et al. | |
| 6,899,890 B2 | 5/2005 | Kirschner et al. | |
| 6,932,810 B2 | 8/2005 | Ryan | |
| 6,949,125 B2 | 9/2005 | Robertson | |
| 6,951,654 B2 | 10/2005 | Malcolm et al. | |
| 6,973,718 B2 | 12/2005 | Sheppard et al. | |
| 6,976,950 B2 | 12/2005 | Connors et al. | |
| 6,988,983 B2 | 1/2006 | Connors et al. | |
| 7,005,138 B2 | 2/2006 | Mahashabde et al. | |
| 7,074,178 B2 | 7/2006 | Connors et al. | |
| 7,521,064 B2 | 4/2009 | Saxena et al. | |
| 7,647,112 B2 | 1/2010 | Tracey et al. | |
| 2003/0059456 A1 | 3/2003 | Malcolm et al. | |
| 2003/0118649 A1 * | 6/2003 | Gao et al. | 424/471 |
| 2003/0118692 A1 | 6/2003 | Wang et al. | |
| 2003/0139800 A1 | 7/2003 | Campbell | |
| 2003/0229263 A1 * | 12/2003 | Connors et al. | 600/29 |
| 2004/0022824 A1 | 2/2004 | Li et al. | |
| 2004/0034332 A1 | 2/2004 | Uhland | |
| 2004/0220552 A1 * | 11/2004 | Heruth et al. | 604/891.1 |
| 2004/0260272 A1 | 12/2004 | Friedman et al. | |
| 2005/0228482 A1 * | 10/2005 | Herzog et al. | 623/1.15 |
| 2005/0234013 A1 | 10/2005 | Parsons | |
| 2005/0234431 A1 | 10/2005 | Williams et al. | |
| 2005/0238733 A1 | 10/2005 | Henry | |
| 2006/0105010 A1 | 5/2006 | Rahe et al. | |
| 2006/0234978 A1 | 10/2006 | Marcum | |
| 2006/0259118 A1 | 11/2006 | Pal et al. | |
| 2006/0264912 A1 * | 11/2006 | McIntyre et al. | 604/891.1 |
| 2007/0172507 A1 | 7/2007 | Zupkas et al. | |
| 2007/0172508 A1 | 7/2007 | Zupkas et al. | |
| 2007/0254014 A1 | 11/2007 | Ahmed et al. | |
| 2008/0051740 A1 | 2/2008 | Sokal et al. | |
| 2009/0004246 A1 | 1/2009 | Woolfson et al. | |
| 2009/0149833 A1 | 6/2009 | Cima et al. | |
| 2009/0247992 A1 | 10/2009 | Shalon et al. | |
| 2010/0003297 A1 | 1/2010 | Tobias et al. | |
| 2010/0152704 A1 | 6/2010 | Lee et al. | |

FOREIGN PATENT DOCUMENTS

| | | | |
|---|---|---|---|
| EP | 0572932 | * | 9/2000 |
| EP | 0572932 A2 | | 4/2007 |
| WO | 9918884 A1 | | 4/1999 |
| WO | 0040234 A1 | | 7/2000 |
| WO | 03/009882 A2 | | 2/2003 |
| WO | WO 03/009882 | * | 2/2003 |
| WO | 2004/037318 A2 | | 5/2004 |
| WO | WO 2004/003718 | * | 5/2004 |
| WO | WO 2004/037318 | * | 5/2004 |
| WO | 2005072751 A1 | | 8/2005 |
| WO | 2005115245 A1 | | 12/2005 |
| WO | 2006/121969 A1 | | 11/2006 |
| WO | 2007021964 A2 | | 2/2007 |
| WO | 2007115259 A2 | | 10/2007 |
| WO | 2009029958 A2 | | 3/2009 |
| WO | 2009076547 A2 | | 6/2009 |
| WO | 2010019507 A2 | | 2/2010 |

OTHER PUBLICATIONS

Bade et al, A placebo-controlled study of intravesical pentosanpolysulphate for the treatment of interstitial cystitis, Br J Urol 79(2): 168-71 (1997).

Collins et al, How common is prostatitis? A national survey of physician visits, J Urol 159(4): 1224-28 (1998).

Curhan et al, Epidemiology of insterstitial cystitis: a population based study, J Urol 161(2): 549-52 (1999).

Grayson et al, Multi-pulse drug delivery from a resorbable polymeric microchip device, Nat Mater 2(11): 767-72 (2003).

Grayson et al, Molecular release from a polymeric microreservoir device: Influence of chemistry, polymer swelling, and loading on device performance, J Biomed Mat Res 69A(3): 502-12 (2004).

Santus & Baker, Osmotic drug delivery: a review of the patent literature, J Controlled Release 35: 1-21 (1995).

Theeuwes, Elementary osmotic pump, J Pharm Sci 64(12): 1987-91 (1975).

Wright et al, DUROS pharmaceutical systems for parenteral & site-directed therapy, Drug Delivery Technology 3 (1) (2003).

Wright & Stevenson, Pumps/Osmotic, Encyclopedia of Controlled Drug Delivery V.2, New York: John Wiley (1999) pp. 909-915.

Parsons et al., Bladder Surface Glycosaminoglycans: An Epithelial Permeability Barrier, J. Urol 143(1): 1932-42 (1990).

Parsons, Successful Downregulation of Bladder Sensory Nerves with Combination of Heparin and Alkalinized Lidocaine in Patients with Interstitial Cystitis, Urology, 65: 45-48 (2005).

Beiko, Urinary Tract Biomaterials, Journal of Urology, vol. 171, 2438-2444, (2004).

Au et al., Methods to Improve Efficacy of Intravesical Mitomycin C: Results of a Randomized Phase III Trial, Journal of National Cancer Institute, Apr. 18, 2001, 597-604, vol. 93-8, Oxford University Press.

Birch et al., Absorption Characteristics of Lignocaine Following Intravesical Instillation, Scand J. of Urology Nephrol, 1994, 359-364, vol. 28, Scandinavian University Press.

Carr et al., Evaluation of a Transoral Delivery System for Topical Anesthesia, The Journal of the American Dental Association, Dec. 2001, 1714-1719, vol. 132, American Dental Association.

Erickson et al., Interstitial Cystitis, Int. Urogynecol J, 1998, 174-183, vol. 9, Springer-Verlag London Ltd.

(56) References Cited

OTHER PUBLICATIONS

Fraser, et al., The Future of Bladder Control—Intravesical Drug Delivery, a Pinch of Pepper, and Gene Therapy, Reviews in Urology, 2002, 1-11, vol. 4, No. 1.
Gammaitoni et al., Safety and Tolerability of the Lidocaine Patch 5%, a Targeted Peripheral Analgesic: A Review of the Literature, The Journal of Clinical Pharmacology, 2003, 111-117, vol. 43, American College of Clinical Pharmacology.
Henry et al., Alkalinized Intravesical Lidocaine to Treat Interstitial Cystitis: Absorption Kinetics in Normal and Interstitial Cystitis Bladders, Urology, Jun. 2001, 119, vol. 57 (Supplemental 6A).
Henry et al., Topical Anesthesia of the Bladder, Abstracts, A61.
Henry et al., Absorption of Alkalized Intravesical Lidocaine in Normal and Inflamed Bladders: A Simple Method for Improving Bladder Anesthesia, The Journal of Urology, Jun. 2001, 1900-1903, vol. 165, American Urological Association, Inc., U.S.A.
Highley et al., Intravesical Drug Delivery Pharmacokinetic and Clinical Considerations, Clinical Pharmacokinet, Jul. 1999, 59-73, vol. 37 (1), Adis International Limited.
Malmstrom, Intravesical Therapy of Superficial Bladder Cancer, Critical Reviews in Oncology Hematology, 2003, 109-126, vol. 47, Elsevier Science Ireland Ltd.
Theoharides et al, Painful Bladder Syndrome/Interstitial Cystitis: Current Concepts and Role of Nutraceuticals, Seminars in Preventive and Alternative Medicine, 2006, 6-14, vol. 2; Elsevier Inc.
Tyagi, et al., Local Drug Delivery to Bladder Using Technology Innovations, Urological Clinics of North America, 2006, 519-530, vol. 33, Elsevier Inc.
Walker et al., Intravesical Chemotherapy: In Vitro Studies on the Relationship Between Dose and Cytotoxicity, Urological Research, 1986, 137-140, vol. 14, Springer-Verlag.
Verma, et al., Formulation Aspects in the Development of Osmotically Controlled Oral Drug Delivery Systems, Journal of Controlled Released, 2002, 7-27, vol. 79, Elsevier Science B.V.
Li et al., Water Based Silicone Elastomer Controlled Release Tablet Film Coating III—Drug Release Mechanisms, Drug Development and Industrial Pharmacy, 1989, 1943-1968, vol. 15(12), Marcel Dekker, Inc.
Thombre et al., Mechanism of Water Transport in Controlled Porosity Osmotic Devices, Journal of Membrane Science, 1989, 279-310, vol. 40, Elsevier Science Publishers B.V.
Stymne et al., Plasma Concentrations of Lignocaine and Prilocaine after a 24-h Application of Analgesic Cream (EMLA®) to Leg Ulcers, British Journal of Dermatology, 2001, 530-534, vol. 145, British Association of Dermatologists.
http://www.ic-network.com/handbook/instill.html, last updated Mar. 16, 2006.
Amark, et al., Follow-Up of Long-Time Treatment with Intravesical Oxybutynin for Neurogenic Bladder in Children, Eur Urol. 1998, 148-153, S. Karger AG, Basel.
Burmeister et al., Intravescial Instillation of Trospium Chloride, Oxybutynin and Verapamil for Relaxation of the Bladder Detrusor Muscle. A Placebo Controlled, Randomized Clinical Test, 1998, Abstract.
Walter, et al., Bioavailability of Trospium Chloride After Intravesical Instillation in Patients with Neurogenic Lower Urinary Tract Dysfunction: A Pilot Study, Neurourology and Urodynamics, 1999, 18:447-453, Wiley-Liss, Inc.
Kim et al., Antimuscarinic Agents Exhibit Local Inhibitory Effects on Muscarinic Receptors in Bladder-Afferent Pathways, 2005, 238-242, Elsevier Inc.
Spratt et al., Clinical Delivery System for Intraperitoneal Hyperthermic Chemotherapy, Cancer Research, Feb. 1980 40:256-260.
Larsson, et al., Effect of Intraperitoneal Instillation of 32% Dextran 70 on Postoperative Adhesion Formation After Tubal Surgery, 1985, Acta Obstet Gynecol Scand 64:437-441.
Jiranantarat et al., Analgesic Effect of Intraperitoneal Instillation of Bupivacaine for Postoperative Laparoscopic Cholecystectomy, J. Med Assoc Thai, Sep. 2002, 85 (Suppl 3): S897-S903.
Grayson, et al. "Molecular Release from a Polymeric Microreservoir Device: Influence of Chemistry, Polymer Swelling, and Loading on Device Performance," Wiley Periodicals, Inc. pp. 502-512 (2004).
Grayson, et al. "Multi-Pulse Drug Delivery from a Resorbable Polymeric Microchip Device," Nature Publishing Group, pp. 1-6 (2003).
Santus, et al. "Osmotic Drug Delivery: A Review of the Patent Literature," J. Controlled Release, pp. 1-21 (1995).
Theeuwes, "Elementary Osmotic Pump, J. Pharmaceutical Sciences," vol. 64.12. pp. 1987-1991 (1975).
Wright, et al., "Implantable Technology," Drug Delivery Technologies, pp. 1-15.
Wright, et al., "Pumps/Osmotic-Introduction," Alzet System, pp. 896-920.
Non-Final Office Action for U.S. Appl. No. 12/709,551 mailed Oct. 20, 2010.
Examination Report for European Patent Application No. 06801285.5 dated Jun. 22, 2010.
Ali, et al., Lidocaine As Endotracheal Tube Cuff Inflating Agent, JAFMC Bangladesh, Jun. 2009, pp. 25-28, vol. 5, No. 1.
Dollo, et al., Endotracheal Tube Cuffs Filled With Lidocaine As a Drug Delivery System in Vitro and in Vivo Investigations, European Journal of Pharmaceutical Sciences, 2001, pp. 319-323, vol. 13, Elsevier Sciences B.V.
Estebe, et al., Alkalinization of Intra-Cuff Lidocaine and Use of Gel Lubrication Protect Against Tracheal Tube-Induced Emergence Phenomena, British Journal of Anaesthesia, 2004, pp. 361-366, vol. 92, No. 3, The Board of Management and Trustees of the British Journal of Anaesthesia.
Estebe, et al., Alkalinization of Intracuff Lidocaine Improves Endotracheal Tube-Induced Emergence Phenomena, Anesth Analg, 2002, pp. 227-230, vol. 94, International Anesthesia Research Society.
Estebe, et al., Alkalinization of Intracuff Lidocaine: Efficacy and Safety, Anesth Analg, 2005, pp. 1536-1541, vol. 101, International Anesthesia Research Society.
Russell, et al., High-performance Liquid Chromatographic Determination of 17β-Estradiol and 17β-Estradiol-3-Acetate Solubilities and Diffusion Coefficients in Silicone Elastomeric Intravaginal Rings, Journal of Chromatography B, 2000, pp. 157-163, vol. 744, Elsevier Science, B.V.
Sconzo, M.D., et al., In Vitro Diffusion of Lidocaine Across Endotracheal Tube Cuffs, Regional Anesthesia, Jan.-Feb. 1990, pp. 37-40.
Woolfson, et al., Design of a Silicone Reservoir Intravaginal Ring for the Delivery of Oxybutynin, Journal of Controlled Release, 2003, pp. 465-476, vol. 91, Elsevier B.V.
Woolfson, et al., Design of an Intravaginal Ring for the Controlled Delivery of 17β-Estradiol as its 3-Acetate Ester, Journal of Controlled Release, 1999, pp. 319-328, vol. 61, Elsevier Science B.V.
International Preliminary Report on Patentability for PCT/US2006/031428.
ADIS R&D Profile, "Oxybutynin Intravesical—Situs, I-Oxy," Drugs R&D 2002; 3 (2): 82-83.
Appell, Rodney A. et al., "339—A Novel Intravesical Device for Optimal Drug Delivery," The Journal of Urology, vol. 163, No. 4, Supplement, Sunday, Apr. 30, p. 77.

\* cited by examiner

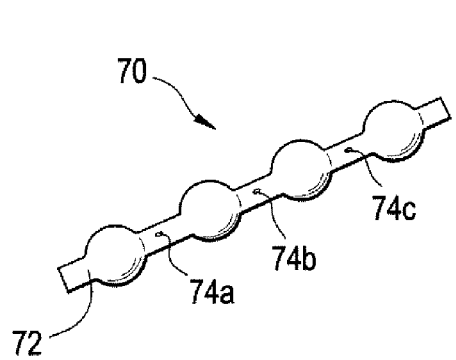
FIG. 7A
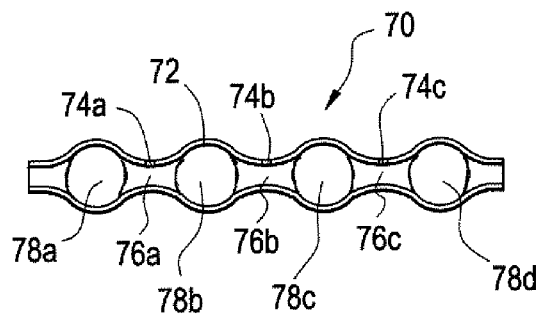
FIG. 7B
FIG. 8
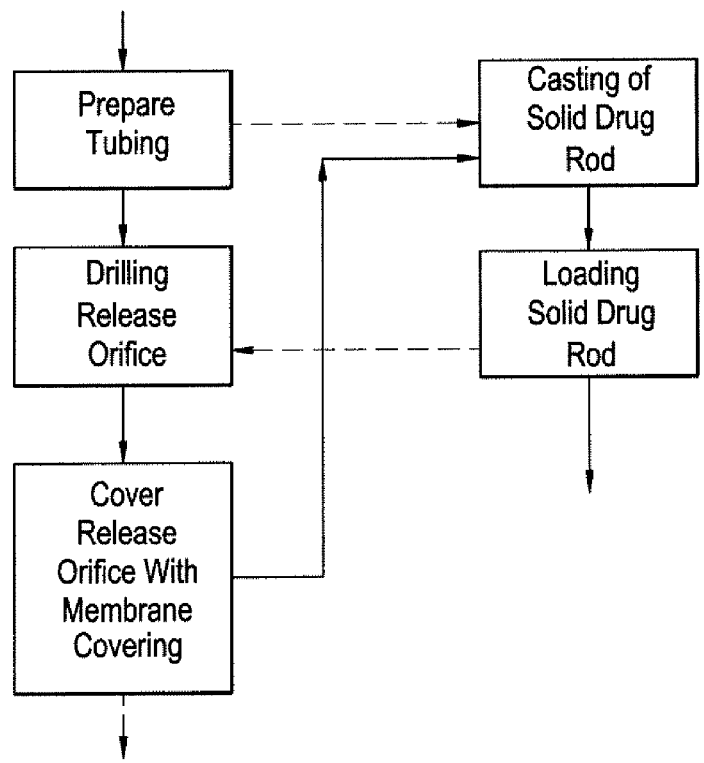

INTRAVESICAL DRUG DELIVERY DEVICE

CROSS REFERENCE TO RELATED APPLICATIONS

This application claims benefit of U.S. Provisional Application No. 60/707,676, filed Aug. 11, 2005, and U.S. Provisional Application No. 60/726,490, filed Oct. 12, 2005. Those applications are incorporated herein by reference in their entirety.

STATEMENT REGARDING FEDERALLY SPONSORED RESEARCH OR DEVELOPMENT

Not applicable.

BACKGROUND OF THE INVENTION

This invention is generally in the field of implantable drug delivery devices, and more particularly to intravesical devices for the controlled release of drug.

Drug delivery is an important aspect of medical treatment. The efficacy of many drugs is directly related to the way in which they are administered. Various systemic methods of drug delivery include oral, intravenous, intramuscular, and transdermal. These systemic methods may produce undesirable side effects and may result in the metabolization of the drug by physiological processes, ultimately reducing the quantity of drug to reach the desired site. Accordingly, a variety of devices and methods have been developed to deliver drug in a more targeted manner, i.e., locally, to address many of the problems associated with systemic drug delivery.

In recent years, the development of microdevices for local drug delivery is one area that has proceeded steadily. Activation of drug release can be passively or actively controlled. Examples of controlled drug delivery devices are disclosed in U.S. Pat. No. 5,797,898, U.S. Pat. No. 6,730,072, U.S. Pat. No. 6,808,522, and U.S. Pat. No. 6,875,208.

These microdevices can be divided roughly in two categories: resorbable polymer-based devices and nonresorbable devices. Polymer devices have the potential for being biodegradable, therefore avoiding the need for removal after implantation. These devices typically have been designed to provide controlled release of drug in vivo by diffusion of the drug out of the polymer and/or by degradation of the polymer over a predetermined period following administration to the patient.

Interstitial cystitis (IC) and chronic prostatitis/chronic pelvic pain syndrome (CP/CPPS) are chronic painful disorders that affect approximately 67 per 100,000 women (Curhan et al., *J. Urol.* 161(2): 549-52 (1999)) and 7 per 100,000 men (Collins et al., *J. Urol.* 159(4); 1224-28 (1998)) in the United States. Both conditions are characterized by chronic pelvic pain, urinary frequency and urgency, and variable degrees of sexual dysfunction. Pentosan polysulfate (PPS) currently is used to treat this condition. However, conventional methods and devices for delivering the drug have significant shortcomings. For example, oral delivery (ELMIRON™, Ortho-Mc-Neil) suffers from low bioavailability, as low as 3% due to a high first pass effect (Parsons et al., *J. Urol.* 153(1): 139-42 (1990)), and causes some mild side effects, such as headaches. PPS delivered intravesically through cystoscopy (with a catheter through the urethra) can provide improved therapeutic effects while reducing the side effects of the drug (Bade et al., *Br. J Urol.* 79(2): 168-71 (1997)). However, the implantation procedure is painful and requires repeating the procedure twice per week for three months. The repetitive nature of this procedure also engendered high risks for urinary tract infection and bacteremia. Thus, a pronounced need exists for an intravesical drug delivery device that will substantially reduce the number of cystoscopic procedures necessary to deliver an effective amount of PPS or other drugs needed for local delivery over an extended period.

Other therapies could benefit from improved intravesical drug delivery devices, particularly where local delivery of a drug to the bladder is preferred or necessary—such as when the side effects associated with systemic delivery of the drug are unbearable and/or when bioavailability from oral administration is too low. For instance, oxybutynin is used for the treatment of overactive bladder syndrome. Currently, oxybutynin is delivered orally or transdermally. Unfortunately, however, approximately 61% of patients taking the drug experience side effects and approximately 7 to 11% of the patients actually stop treatment due to the severity of the side effects.

Situs Corporation developed an intravesical drug delivery system (UROS infuser device) for the delivery of pharmaceutical solutions of drugs, such as oxybutynin (for the treatment of overactive bladder) and mitomycin C (for the treatment of bladder cancer). The UROS infuser device and methods of making and implanting the device are described in U.S. Pat. No. 6,171,298, No. 6,183,461; and No. 6,139,535. The UROS infuser device has an elastomeric outer tubing and contains inextensible wire which connects both inner ends. The device has a linear shape during the cystoscopic insertion into the bladder, changes to a crescent shape following implantation and filling of the device with the pharmaceutical solution, and returns to a linear shape after releasing all of the pharmaceutical solution. Extended release of the pharmaceutical solution is controlled by means of a pressure-responsive valve and/or flow-resistive element inside the tubing. The size of the UROS infuser device depends on the size of each inner component, and a considerable portion of the inner volume is used to contain the mechanical components, not drug solution. With a length of approximately 10 cm and an outer diameter of approximately 0.6 cm, the large size of the UROS infuser device can cause significant discomfort and pain to patients, particularly during urological deployment and retrieval of the device. The UROS infuser device also requires an additional surgical procedure for loading of the pharmaceutical solution into the device following implantation. Accordingly, a need exists for an intravesical drug delivery device that is smaller in size, to avoid unnecessary discomfort and pain in patients. In addition, it would be desirable to provide an intravesical drug delivery device that can minimize the number of surgical procedures required for implantation and delivery of drug over the treatment period.

SUMMARY OF THE INVENTION

Drug delivery devices for intravesical administration and local drug delivery are provided. In one aspect, the device has a body which comprises at least one hollow tube having an outer surface, an inner surface, and at least one reservoir defined within the hollow tube; a drug formulation (which includes a drug) contained in the reservoir; and one or more apertures providing a passageway to release the drug from the drug delivery device. The apertures may be through the sidewall of the tube or through an end of the tube. The diameter of each aperture preferably is between about 20 μm and about 300 μm. The hollow tube may be formed of a water permeable material. The device is configured to permit its insertion into a body cavity and its retention in the body cavity during release of the drug.

In one embodiment, the hollow tube is elastomeric so that the tube can be elastically deformed to permit intravesical insertion of the drug delivery device. The construction material permits the device to be elastically deformed from its initial shape into an elongated shape for passage through a catheter. Following passage through a catheter, the device can return to or toward its initial shape which facilitates retention of the device in a body cavity. In another embodiment, the body has a narrow, elongated shape effective to permit insertion of the drug delivery device through a catheter, without necessarily deforming the body, and into a body cavity, and the body includes a one or a plurality of flexible projections that facilitate retention of the device within the body cavity. In various embodiments, the hollow tube may both have elastomeric materials of construction and include flexible projections for retention.

In one embodiment where the hollow tube is elastomeric, the tube has an annular shape, which may be, for example, elliptical or toroidal. In other embodiments, the tube has a linear or cylindrical profile. In the linear embodiment, the device's aperture may be located in an orifice structure disposed in one end of the at least one hollow tube. The device may include two or more hollow tubes connected together in a linear fashion. In one embodiment, the hollow tube has an inner diameter between about 300 μm and about 500 μm and an outer diameter between about 600 μm and about 900 μm.

In one embodiment, the body of the device further includes a retrieval feature, to facilitate grasping of and removal of the device from the body cavity, particularly if the device is non-resorbable. The retrieval feature may be, for example, a coil, ring, or pig tail extending from one or more ends of the device.

The tube may be constructed of a resorbable or non-resorbable material. In one embodiment, the tube is made of a biocompatible polymer, such as a silicone. In one embodiment, the device includes a radio-opaque material, which may be a filler material included in the tube.

In one embodiment, the device includes a plurality of apertures in spaced positions in the sidewall of the hollow tube. The tube may include two or more reservoirs, where each reservoir is defined by the inner surface of the tube and at least one partition. Each reservoir may have one aperture or two or more apertures. The partition may include a polymeric material, which may be resorbable. The partition may be in the form of a spheroidal object.

In one embodiment, the device further includes a degradable membrane disposed over or in each of the one or more apertures to control the time of release of the drug. The degradable membrane may be formed of biodegradable polymer material, and may have a thickness between about 145 μm and about 160 μm.

In one embodiment, the drug formulation is in a solid or semi-solid form. In one embodiment adapted for use in the bladder, the drug formulation and dose are effective for treating overactive bladder syndrome, bladder cancer, or interstitial cystitis. In various embodiments, the drug formulation comprises a drug selected from the group consisting of lidocaine hydrochloride, glycosaminoglycans, pentosan polysulfate, dimethyl sulfoxide, chondroitin sulfate C, oxybutynin, mitomycin C, or a combination thereof. The drug formulation may include an anesthetic, an analgesic, an antibiotic, or a combination thereof. The drug formulation may further include one or more pharmaceutically acceptable excipients.

In another aspect, a method is provided for administering a drug to a patient. The method includes implanting one of the drug delivery device described herein into a body cavity of a patient; and then releasing the drug into the body cavity from the drug delivery device. In one embodiment, the body cavity is the bladder and the implantation is performed by passing the intravesical drug delivery device through a catheter inserted into the urethra. This method may be useful, for example, for treating interstitial cystitis, overactive bladder syndrome, or bladder cancer.

In another aspect, a method of making an implantable drug delivery device is provided. In one embodiment, the method includes sealing a material, which comprises a drug, within a hollow tube formed of a biocompatible material, which may be water permeable; providing one or more apertures in the hollow tube, in the sidewall of the tube, at an end of the tube, or in both the sidewall and an end, to form an intravesical drug delivery device; and providing that the intravesical drug delivery device is configured to have a first shape capable passing through a catheter for deployment in a body cavity and then to take a second shape that facilitates retention of the device with the body cavity. The step of forming one or more apertures may include laser drilling one or more holes in the sidewall of the tube. The laser drilling may occur before or after the step of loading the tube with the drug-comprising material. In one embodiment, the step of sealing the drug-comprising material in the tube includes a first sub-step of loading into the tube a drug dissolved or dispersed in a liquid medium, and a second step of removing the liquid medium to form a solid or semi-solid rod. The method may further include the step of forming a degradable membrane over or in each of the one or more apertures to control the time of release of the drug therethrough.

BRIEF DESCRIPTION OF THE DRAWINGS

FIG. 7A is a perspective view illustrating one embodiment of a drug delivery device having a linear shape with spherical partitions for creating a plurality of discrete reservoirs. FIG. 7B is a cross-sectional view of the drug delivery device of FIG. 7A.

FIG. 8 is a process flow diagram illustrating a method for making a drug delivery device.

DETAILED DESCRIPTION OF THE INVENTION

Figure 1A:
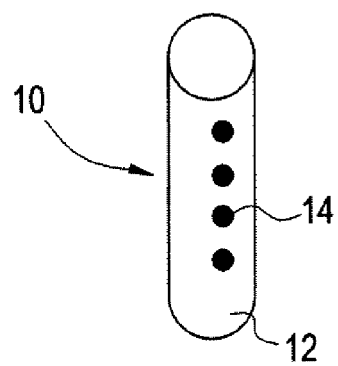
FIGS. 1A and 1B are plan views of embodiments of a drug delivery device having a linear shape.

Improved intravesical drug delivery devices have been developed. The tiny devices are particularly suited for delivery into a body cavity such as the bladder. The device provides controlled, site specific delivery of a drug formulation over an extended period of time. The device can be tailored to release one or more drugs in a preprogrammed manner, for therapies requiring bolus (one-time), pulsatile, or constant drug delivery.

The device advantageously addresses many of the deficiencies described above for conventional devices intended for cystoseopic implantation and drug delivery to the bladder. The present device can be implanted once and release several doses of drug over an extended period, without requiring surgery or frequent interventions (such as to re-fill the drug reservoir of a conventional device). By limiting the number of procedures required to be performed on the patient during the treatment process, the present local drug delivery system can improve both the quality of life of the patient during the treatment process and avoid potential side effects associated with systemic administration of the drug.

I. The Intravesical Drug Delivery Device

In one aspect, the drug delivery device for intravesical administration includes a body which comprises at least one tube having an outer surface, an inner surface, and at least one reservoir defined within the tube. A drug formulation is contained in the reservoir. The tube has one or more apertures through which the drug is released.

In a preferred embodiment, the device operates essentially as an osmotic pump. Following implantation, water permeates through the tube body, enters the reservoir, and is imbibed by the drug formulation. Solubilized drug is dispensed at a controlled rate out of the device through the one or more apertures, driven by osmotic pressure in the reservoir. The delivery rate can be predicted from the physicochemical parameters defining the particular drug delivery system, according to well known principles, which are described for example in Theeuwes, *J. Pharm. Sci.*, 64(12):1987-91 (1975). In an alternative embodiment, the device operates essentially by diffusion of the drug through one or more apertures.

In one embodiment, the tube is formed of an elastomeric material so that the tube can be elastically deformed to permit intravesical insertion of the drug delivery device. For instance, one embodiment of the device can be elastically deformed from its initial shape into a tubular shape for passage through a catheter, and following passage through the catheter the device returns to its initial or expanded shape which facilitates retention of the device in a body cavity.

In one embodiment, a degradable membrane may be disposed over or in each of the one or more apertures to control the time of release of the drug formulation. That is, the time at which release is initiated.

The Device Body

The intravesical drug delivery device can be made to be completely or partially resorbable so that no explantation of the device is required following release of the drug formulation. As used herein, the term "resorbable" means that the device, or part thereof, degrades in vivo by dissolution, enzymatic hydrolysis, erosion, or a combination thereof. This degradation occurs at a time which does not interfere with the intended kinetics of release of the drug from the device, e.g., substantial resorption of the device body would not occur until after the drug formulation is substantially or completely released. Alternatively, the intravesical drug delivery device can be at least partially non-resorbable, such that the device body can be removed following release of the drug formulation. The device need not be completely resorbable; for example, it could be made partially resorbable so that the device, upon partial resorption, falls apart into non-resorbable pieces small enough to be excreted from the bladder. Useful biocompatible resorbable and non-resorbable materials of construction are known in the art.

The exact configuration and shape of the intravesical drug delivery device may be selected depending upon a variety of factors including the specific site of implantation, route of implantation, drug, dosage regimen, and therapeutic application of the device. Preferably, the design of the device will minimize the patient's pain and discomfort, while delivering a therapeutically effective dose of the drug locally to the patient.

In one embodiment the device body includes one or more annular portions. For instance, the tube may be in the shape of a torus or elliptical ring. This design is especially advantageous for urological deployment and retrieval of the device. The diameter of the torus will be larger than the internal urethral orifice to avoid accidental voiding. This device can be delivered cystoscopically because of its elastomeric nature. In another embodiment, the tube may be linear, e.g., in a substantially cylindrical shape.

The hollow tube of the device body preferably is cylindrical, i.e., has a circular cross-section; however, other cross-sectional shapes of the tube are envisioned (e.g., square, triangle, hexagon, and other polygons). The body of the intravesical drug delivery device may include one tube or a plurality of connected tubes. The hollow tube could have various shapes and configurations; in one case, the device body could have a hollow tube formed from a plurality hollow beads strung together in a linear arrangement.

Two or more tubes may be connected together in a linear fashion. This may be done to increase the amount of drug loading. The cystoscopic deployment and retrieval of the device through urethra is possible because each O-ring can be deformed like a single O-ring configuration. Attachment of multiple O-rings can be done by medical grade silicone adhesive or other means known in the art. Another way to produce this type of design is by a casting method, i.e., pouring curing silicone into a mold.

Figure 1B:
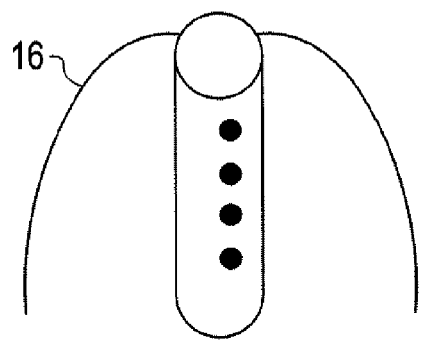

FIGS. 1A-B show one embodiment of an intravesical drug delivery device having a body that comprises a linear tube. Device 10 include a body which comprises a tube 12. An array of apertures are disposed in the tube and closed off by degradable timing membranes 14. The ends of the tube may be sealed using a medical grade silicone adhesive, a partition structure (e.g., a microbead) as described below, or a combination thereof. Flexible projections 16 extend from the device body and facilitate retention of the device in a body cavity.

Figure 2A:
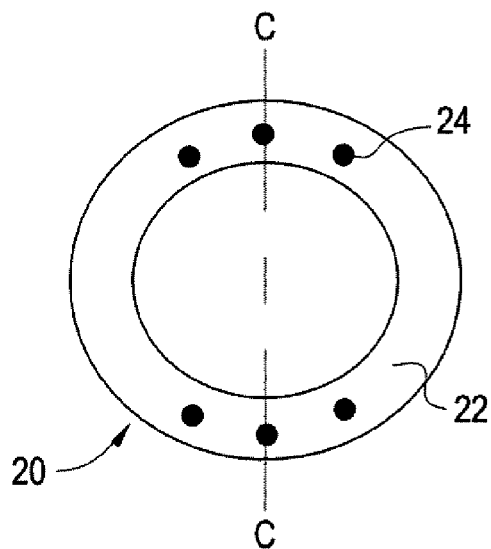
FIG. 2A is a plan view of one embodiment of a drug delivery device having an o-ring shape.
Figure 2B:
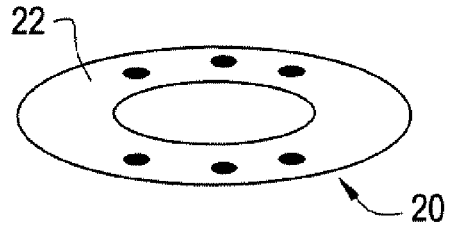
FIG. 2B is a plan view illustrating the drug delivery device of FIG. 2A in a compressed configuration for permitting the device to be passed into a body cavity.
Figure 2C:
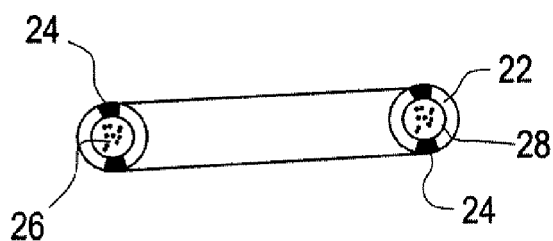
FIG. 2C is a cross-sectional view of the device of FIG. 2A taken along line C-C.

FIGS. 2A-C show one embodiment of an intravesical drug delivery device having a body that comprises a single annular tube. Device 20 include a body which comprises a toroidal tube 22. An array of apertures are disposed in the tube and filled with degradable timing membranes 24. Reservoir 28 is loaded with drug formulation 26. FIG. 2B shows the device in a compressed form suitable for deployment through a catheter.

Figure 3A:
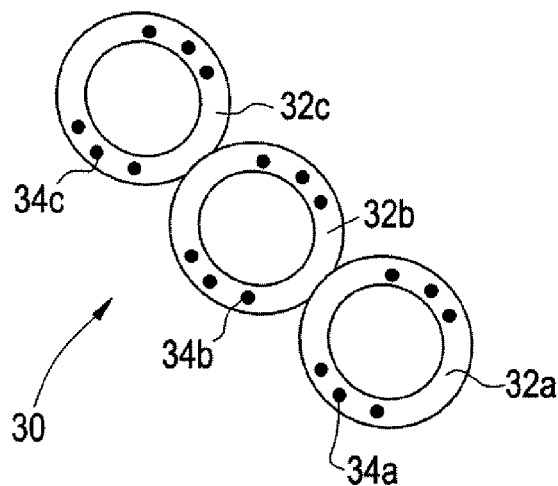
FIG. 3A is a plan view of one embodiment of a drug delivery device having a series of connected torus shapes.
Figure 3B:
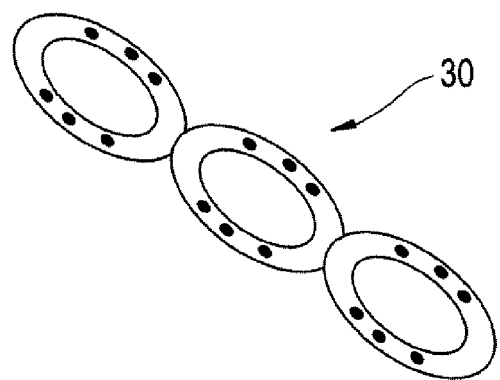
FIG. 3B is a plan view illustrating the drug delivery device of FIG. 3A in a compressed configuration for permitting the device to be passed into a body cavity.

FIGS. 3A-B show one embodiment of an intravesical drug delivery device having a body that comprises three connected annular tubes. Device 30 include a body which comprises three toroidal tubes 32a, 32b, 32c. An array of apertures are disposed in each tube and covered by discrete degradable membranes 34a, 34b, 34c. FIG. 3B shows the device in a compressed form suitable for deployment through a catheter.

Figure 4:
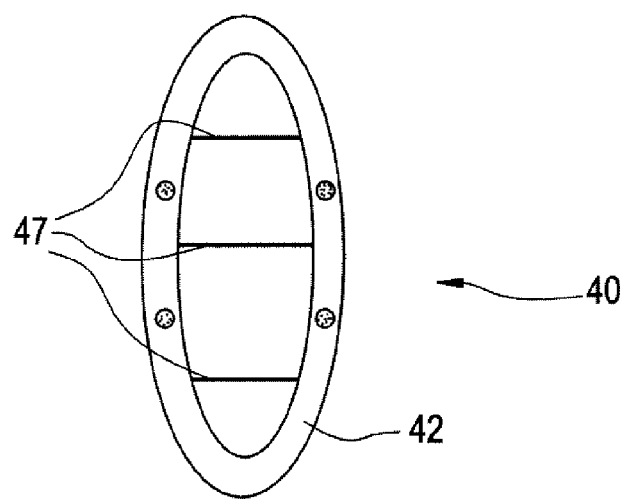
FIG. 4 is a plan view of one embodiment of a drug delivery device having an elliptical shape.

An oval shape of the device can help prevent the membrane rupture because the orifice membranes undergo less strain during urological insertion and deployment of the elastic device. The oval shape is also advantageous during the endoscopic retrieval by grasping instruments, as it provides a clear point of where the device should be grasped to fold back into the catheter. The elliptical device can be made by adopting silicone molding method or more conveniently by introducing strings to toroidal body. In one embodiment, the annular tube is connected with strings for maintaining an oval shape. After deployment of the device, the O-ring is restricted from recovering its initial circular shape by the strings. FIG. 4 shows one embodiment of an intravesical drug delivery device 40 having a body that comprises a single annular tube 42 that is constrained into an elliptical shape with a plurality of inextensible strings 47.

In another embodiment, a connecting component is inserted into one or both ends of the O-ring device. Alternatively, the connection can be done by medical grade silicone adhesives and/or by a silicone connecting component. Drug will be loaded only at the middle section. The closed section(s) at the end(s) can be used to facilitate the endoscopic device retrieval and promote the buoyancy of the device in the bladder.

In a preferred embodiment, the device body is made of a biocompatible, water permeable material known in the art. The device body alternatively may be substantially water impermeable. In a preferred embodiment, the material is an elastomeric material. In one embodiment, the device body is non-resorbable. In one embodiment of non-resorbable device, the tube of the body is formed of a medical grade silicone tubing, as known in the art. Other examples of suitable non-resorbable materials include synthetic polymers selected from poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene) and other fluorinated polymers, poly(siloxanes), copolymers thereof, and combinations thereof. In another embodiment, the device body is resorbable. In one embodiment of resorbable device, the tube of the body is formed of a biodegradable or bioerodible polymer. Examples of suitable resorbable materials include synthetic polymers selected from poly(amides), poly(esters), poly(anhydrides), poly(orthoesters), polyphosphazenes, pseudo poly(amino acids), copolymers thereof and mixtures thereof. In a preferred embodiment, the resorbable synthetic polymers are selected from poly(lactic acids), poly(glycolic acids), poly(lactic-co-glycolic acids), poly(caprolactones), and mixtures thereof.

The size of a urological device, or other implant device, is important. The smaller the device, the less pain and discomfort the patient will experience during insertion and use of the device, and particularly during cystoscopic implantation of the device. In a preferred embodiment, the device body has a length of about 1 cm to about 10 cm, and when in its shape for insertion it has an effective outer diameter (or largest cross-sectional dimension) of about 0.05 cm to 0.07 cm. (A 10 cm length device forms a ring with a diameter of 3.18 cm.) In one embodiment, the inner surface of the tube has a diameter between about 300 μm and about 500 μm, and the outer surface of the tube has an diameter between about 600 μm and about 900 μm.

The rate and total amount of drug delivered from a single device will depend, for example, on the surface area of the body of the device and the permeability of the materials of construction of the body of the device, as well as the number of apertures employed and the total mass of drug load. Given a particular target therapeutic dosage of a drug and acceptable implant dimensions for a particular body cavity and route of implantation, one skilled in the art can select appropriate materials of construction and an appropriate structural design for the device and drug formulation using known theoretical calculations and/or routine experimentation.

In one embodiment, the device body (e.g., the silicone tubing) can be partially or wholly coated with a coating material, for example to modulate (e.g., reduce) water permeability of the device body and thus control (e.g., slow) the rate of release of the drug from the device. For example, the coating material may be a parylene coating, curable silicone coating, or another biocompatible coating material known in the art. The coating thickness can be varied on a particular device, so that certain parts of the device body have a higher or lower water permeability relative to other parts of the device body. In one case, with a multi-reservoir device containing different drugs in the each reservoir, the tube around a first reservoir may be coated with a first coating material of a first thickness, while the tube around a second reservoir may be uncoated, coated with a second (different) coating material, or coated with the first coating material but at a second (different) thickness.

In a preferred embodiment, the tube preferably includes at least one radio-opaque portion or structure to facilitate detection or viewing of the device as part of the implantation or explantation procedure. In one embodiment, the tube is constructed of a material that includes a radio-opaque filler material, such as barium sulfate or another radio-opaque material known in the art.

Silicone tubing may be made radio-opaque (for X-ray imaging or fluoroscopy) by blending radio-opaque fillers, such as barium sulfate or other suitable materials, during the processing of the tubing. Ultrasound imaging can also detect silicone in vivo, but it may suffer from lack of resolution to be able to correctly image our device if the latter is kept small. Fluoroscopy may be the preferred method during deployment/retrieval of the non-resorbable device by providing accurate real-time imaging of the position and orientation of the device to the practitioner performing the procedure.

Drug Reservoir

The tube or tubes of the device body include at least one reservoir for containing the drug formulation. In one embodiment, an interior space in a tube is partitioned into two or more separate reservoirs. Multiple apertures may either share a common drug reservoir or have separate reservoirs. Such a multi-reservoir device is useful in at least two particular types of device embodiments: (1) when two or more separate drug formulations are to be delivered from a single device, or (2) when a single drug is to be delivered at two different rates or at different times following implantation, such as when a first dose of the drug is pre-programmed to release at a first time and a second dose is pre-programmed to release at a second, later time. This different pre-programming can be achieved by using different timing membranes for the different reservoirs, for instance with two or more reservoirs, the reservoirs being defined by the inner surface of the tube and at least one partition. The partition structure in the tube may be in the form of a spheroidal object, such as a ceramic bead or other microsphere. The partition structure also may be in the shape of a disk or cylinder. The partition may be non-resorbable or resorbable. In one embodiment, the partition structure is made of a biocompatible polymeric material, such as a biodegradable or bioerodible polymer.

FIGS. 7A-B show intravesical drug delivery device 70 which has a body that includes linear tube 72. The hollow space in the tube is partitioned into three reservoirs 76a, 76b, 76c, each of which has a single corresponding aperture 74a, 74b, 74c. The reservoirs are defined by the inner surface of the tube (i.e. the tube sidewall) and by spherical partition structures 78a, 78b, 78c, 78d spaced within the interior space of the tube. As can be seen, the partition structures are secured in place within the tube by having a larger diameter than the inner diameter of the unstretched elastomeric tube, which causes the tube to stretch and snugly fit around the partition structures, sealing each reservoir.

Partitioned reservoirs can prevent the aperture with a faster biodegradable membrane from monopolizing most of the loaded drug material and leaving only a little of the drug meant for subsequent release orifices. A separate reservoir for each release aperture will thus maximize the effect of multiple biodegradable timing membranes.

In a preferred embodiment, the total volume of the reservoir (or combined reservoirs) is sufficient to contain all of the drug needed for local delivery over the course of a single therapy. That is, it desirably contains all of the doses of drug anticipated, so that multiple cystoscopic procedures are not needed, or are reduced in number/frequency to complete the therapy prescribed for a given disease or condition.

Apertures

In one embodiment, the device body includes one or more apertures through the sidewall of the at least one tube, as illustrated for example in FIGS. 1-7.

Figure 14:
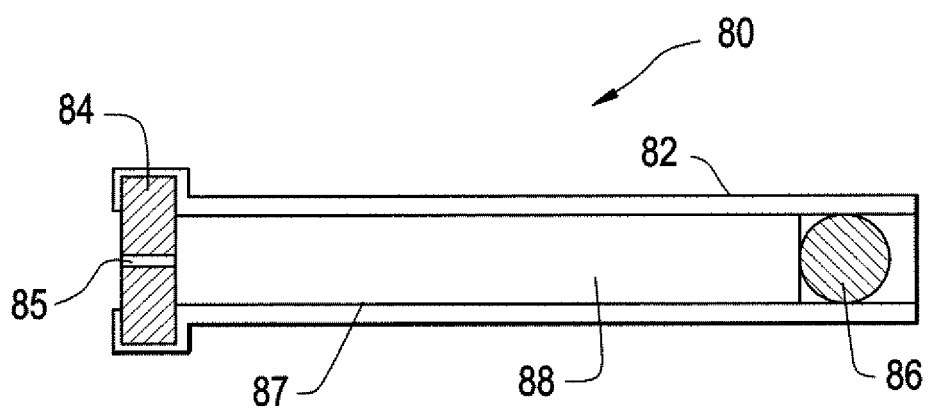
FIG. 14 is a cross-sectional view of one embodiment of a drug delivery device having a linear shape with a precision orifice plugging one end of the central bore in a tubular silicone body and a microbead plugging the opposing end, with a drug formulation disposed in the reservoir defined therebetween.

In another embodiment, the device body includes one or more apertures in an orifice structure disposed in the end of a linear tube structure, as illustrated in FIG. 14. FIG. 14 shows drug delivery device 80 having a tubular silicone body 82 with a precision orifice structure 84 (with aperture 85) plugging one end of the central bore of the body and a microbead 86 plugging the opposing end with a drug formulation 88 disposed in the reservoir 87 defined between the orifice structure and the microbead. The orifice structure may be a precision orifice known in the art (available for example from Bird Precision Orifices, Swiss Jewel Company). The orifice can be inserted within and/or attached to the silicone tubing with silicone adhesives. In one example, the device may include silicone tubing having an inner diameter of 305 µm and outer diameter of 635 µm, with a precision orifice structure made of ruby or sapphire and having an outer diameter of about 1.5 mm or smaller.

The one or more apertures provide a passageway to release the drug formulation from the drug delivery device. In one embodiment, the device includes an array of two or more discrete apertures in spaced positions in the tube. The two or more apertures may be in fluid communication with a single reservoir or with a plurality of reservoirs. The placement of apertures near the portion of the tube which will be folded during cystoscopic insertion is avoided in order to prevent the possible tear of polymer biodegradable membranes on the apertures.

The size of the aperture is important in providing a controlled rate of release of the drug. Where the device operates as an osmotic pump, it should be small enough to minimize the contribution to the delivery rate made by diffusion of the drug through the aperture, yet the aperture should be large enough to minimize hydrostatic pressure within the reservoir, which pressure undesirably would tend to decrease the osmotic flux and/or cause the reservoir volume to increase. Within these constraints on aperture size, one may then vary the number of such sized apertures employed in a single device (or in a single reservoir) in order to provide a needed total rate of drug released. In exemplary embodiments, the diameter of the aperture is between about 20 µm and about 300 µm (e.g., 20 to 100 µm, 25 to 75 µm, etc.). Where the device operates primarily by a diffusion mechanism, apertures may be in this range or larger.

A single device may have apertures of two or more different sizes. The aperture typically is circular in shape, although other shapes are possible and envisioned, and will typically depend on manufacturing considerations.

In one embodiment, the apertures in the wall of the silicone tubing are drilled by laser ablation and then are covered with biodegradable timing membranes. The capability of drilling well-defined holes into medical grade polymers is known, and a hole can be drilled with a diameter as small as 0.050 mm and through-hole drilling as well as depth-controlled drilling is possible. Silicone drilling by laser ablation can therefore be achieved before or after drug loading into the tubing.

Degradable Membranes

The one or more apertures have a degradable membrane disposed over or in each of the apertures, to control the time at which release of the drug formulation begins. In one embodiment, the degradable membrane is in the form of a uniform coating covering the outer surface of the tube of the device body. In another embodiment, the discrete degradable membranes are provided substantially within the aperture. Combinations of two or more degradable membranes may be used to control release from one aperture.

The thickness of the degradable membrane in a particular system will depend for example on the chemistry and mechanical properties of the material of construction selected for the degradable membrane (which primarily govern the rate of degradation), as well as on the desired time of delay of drug release for the particular drug delivery device. See, e.g., Richards Grayson, et al., "Molecular release from a polymeric microreservoir device: Influence of chemistry, polymer swelling, and loading on device performance" Wiley InterScience (6 Apr. 2004); Richards Grayson, et al., "Multi-pulse drug delivery form a resorbable polymeric microchip device" Nature Materials, Advance Online Publication (19 Oct. 2003); U.S. Pat. No. 6,808,522. In one embodiment the degradable membrane has a thickness between about 100 µm and about 200 µm, such as between 145 µm and 160 µm.

The membranes are formed of a biocompatible material. In one embodiment, the membranes are formed of a resorbable synthetic polymer such as polyester, a poly(anhydride), or a polycaprolactone. In another embodiment, the membranes are formed of a resorbable biological materials such as cholesterol, other lipids and fats.

For embodiments of these devices in which it is desired to release drug over a short period of time, the degradable membrane may be fabricated from quickly disintegrating materials including, for example, poly(lactide-co-glycolide) copolymers containing a high glycolide content, copolymers of poly(lactones) with fast degradation times, certain poly (anhydrides), hydrogels, oligosaccharides, and polysaccharides. For applications in which a longer or delayed release time is desirable, the degradable membrane may be fabricated from materials that take longer to disintegrate, for example, a resorbable biological materials such as cholesterol, other lipids and fats, and lipid bilayers, polymers such as poly(caprolactone) or certain poly(anhydrides), and PLGA copolymers with high lactic acid content.

Complex release profiles can be provided from a single drug delivery device. In one embodiment, this may be accomplished by having different membranes over different apertures, either to the same reservoir or different reservoirs. In one case, one of the membranes is formed of a first material and the other of the at least membranes is formed of a second material, wherein the first material has a different degradation rate in vivo compared to the second material. In another case, one of the membranes has a first thickness and the other of the at least two membranes has a second, greater thickness. These approaches may be mixed and matched to design a particular release profile, alone or in combination with kinetics altering approaches based on formulating the drug with a release controlling excipient material, as described below.

The Drug Formulation

The drug formulation can include essentially any therapeutic, prophylactic, or diagnostic agent that would be useful to deliver locally to a body cavity. The drug formulation may consist only of the drug, or may include one or more pharmaceutically acceptable excipients.

In a preferred embodiment, the drug formulation is in a solid or semi-solid form in order to reduce the overall volume of the drug formulation and thereby minimize the size of the device—to promote ease of implantation. In many embodiments, the drug formulation desirably includes no or a minimum quantity of excipient for the same reasons of volume/size minimization.

In other embodiments, the drug formulation may be in the form of a liquid, solution, suspension, emulsion, emulsions, colloidal suspensions, slurries, gel mixtures such as hydrogels, or combination thereof. The drug formulation may be in a powder or microparticle form, for example, as a hydratable or water soluble solid.

Pharmaceutically acceptable excipients are known in the art and may include viscosity modifiers, bulking agents, surface active agents, dispersants, osmotic agents, diluents, and other non-active ingredient of the formulation intended to facilitate handling, stability, dispersibility, wettability, and/or release kinetics of the drug (i.e., the active pharmaceutical ingredient or diagnostic agent).

In a preferred embodiment, the present intravesical drug delivery device is used to treat inflammatory conditions such as interstitial cystitis, prostatitis, and urethritis. Representative examples of specific drugs for these conditions include lidocaine hydrochloride, glycosaminoglycans (e.g., chondroitin sulfate, sulodexide), pentosanpolysulfate, dimethyl sulfoxide (DMSO), oxybutynin, mitomycin C, heparin, flavoxate, or a combination thereof.

In another embodiment, the intravesical drug delivery device is used to provide pain relief to the patient. A variety of anesthetic agent, analgesic agents, and combinations thereof may be used. Representative examples of suitable such agents include lidocaine hydrochloride, procaine hydrochloride, salicyl alcohol, tetracaine hydrochloride, phenazopyridine hydrochloride, acetaminophen, acetylsalicylic acid, flufenisal, ibuprofen, indoprofen, indomethacin, naproxen, codeine, oxycodone, and fentanyl citrate.

The present intravesical drug delivery device can be used to treat urinary incontinence, including urge incontinence and neurogenic incontinence. Drugs that may be used include anticholinergic agents, antispasmodic agents, anti-muscarinic agents, β-2 agonists, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In another embodiment, the present intravesical drug delivery device is used to treat urinary tract cancer, such as bladder cancer and prostate cancer. Drugs that may be used include antiproliferative agents, cytotoxic agents, chemotherapeutic agents, or a combination thereof. Representative examples of suitable drugs for the treatment of urinary tract cancer include Bacillus Calmette Guerin (BCG) vaccine, cisplatin, doxorubicin, methotrexate, vinblastine, thiotepa, mitomycin, fluorouracil, leuprolide, flutamide, diethylstilbestrol, estramustine, megestrol acetate, cyproterone, flutamide, and cyclophosphamide. The drug treatment may be coupled with a conventional radiation or surgical therapy targeted to the cancerous tissue.

In still another embodiment, the present intravesical drug delivery device is used to treat infections involving the bladder, the prostate, and the urethra. Antibiotics, antibacterial, antifungal, antiprotozoal, antiviral and other antiinfective agents can be administered for treatment of such infections. Representative examples of suitable drugs for the treatment of infections include mitomycin, ciprofloxacin, norfiloxacin, ofloxacin, methanamine, nitrofurantoin, ampicillin, amoxicillin, nafcillin, trimethoprim, sulfa, trimethoprimsulfamethoxazole, erythromycin, doxycycline, metronidazole, tetracycline, kanamycin, penicillins, cephalosporins, and aminoglycosides.

Other drugs and excipient may be used for other therapies and at other non-bladder body cavity sites. Combinations of two or more drugs, stored in (and released from) the same or separate reservoirs in the device are envisioned.

The excipient of the drug formulation may be a matrix material, selected to modulate or control the rate of release of the drug from the reservoir. In one embodiment, the matrix material may be a resorbable or non-resorbable polymer as described above. In another embodiment, the excipient comprises a hydrophobic or amphiphilic compound, such as a lipid (e.g., selected from fatty acids and derivatives, mono-, di and triglycerides, phospholipids, sphingolipids, cholesterol and steroid derivatives, oils, vitamins and terpenes), The drug formulation may provide a temporally modulated release profile or a more continuous or consistent release profile. Pulsatile release can be achieved from a plurality of reservoirs. For example, different degradable membrane can be used to by temporally stagger the release from each of several reservoirs.

Other Device Features

In one embodiment, the body of the intravesical drug delivery device further includes one or more flexible projections that facilitate retention of the device in a body cavity. These anchoring structures may be in the form or one, two, three, or more "wing-like" or "leg-like" structures which can be folded against the device body to provide a narrow device profile during insertion (or retrieval) of the device, but which will expand into an extended formation (or otherwise return to its principal uncompressed state) following implantation to prevent inadvertent release (e.g., voiding) of the device from the bladder or other body cavity. See FIG. 1B.

In one embodiment, the body of the intravesical drug delivery device further includes at least one retrieval feature. The retrieval feature is a structure that facilitates removal of the device from the body cavity, for example for removal of a non-resorbable device body following release of the drug formulation. Representative examples of retrieval features include coils, rings, pig tails, and the like. The retrieval feature typically is provided at an end portion of the device when the device is in an folded or compressed form for explantation, to facilitate folding or compression to pull the device into an opening in a catheter.

The device can be retrieved by conventional endoscopic grasping instruments. Endoscopic manipulative instruments such as alligator forceps, three or four-pronged optical graspers can be used to remove the device out of the bladder when the retrieval is needed. If the device has an O-shaped or coiled portion, the removal of the device can be facilitated by those grasping instruments. Especially, an O-ring shaped device is advantageous during endoscopic retrieval due to its symmetrical shape.

Figure 5A:
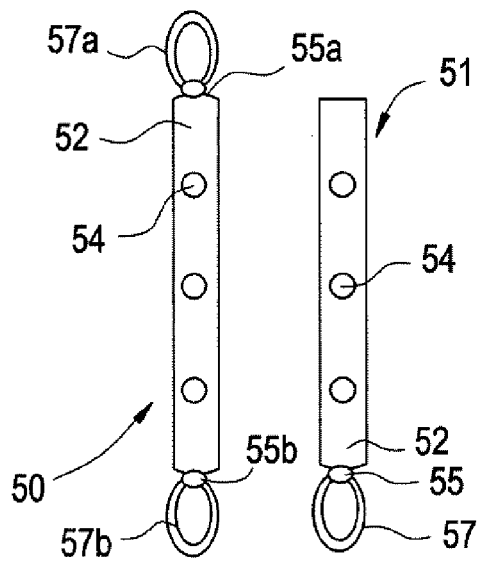
FIGS. 5A and 5B are plan views showing various embodiments of a drug delivery device having retrieval rings on one or both ends of the device.
Figure 5B:
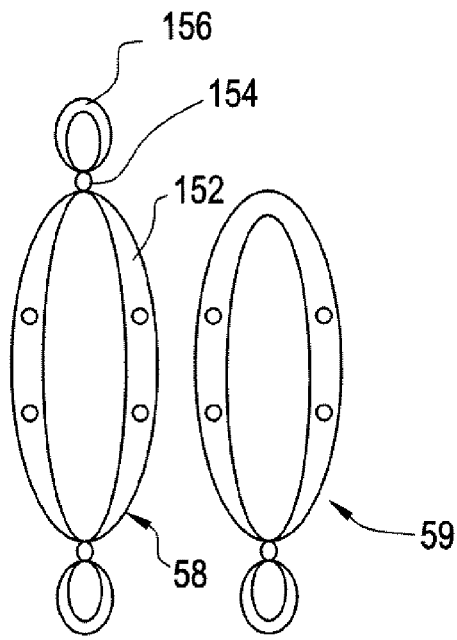

FIGS. 5A-B show various linear and annular body devices with retrieval rings provided on one or both ends of the elongated drug delivery devices. Device 50 include a body which comprises a linear tube 52. An array of apertures are disposed in the tube and closed off by degradable timing membranes 54. Retrieval rings 57a, 57b are attached to the opposing ends of the tube with securement means 55a, 55b, respectively. The securement means may be, for example, a silicone adhesive. Device 51 is similar to device 50, but includes a single retrieval ring 57 attached by securement means 55 at one end of the tube 52. Devices 58 and 59 are similar to devices 50 and 51, respectively, but have an annular tube shaped body rather than a linear shaped body and a different securement means. Elliptical annular tube 152 is pinched with constriction component 154 to form a retrieval ring 156 from the same tubular body. For example, the constriction component could be a band or bead having a hole through which a portion of the tube is pulled or threaded. The constriction component would be made of a biocompatible material, which may be elastic or rigid.

Figure 6:
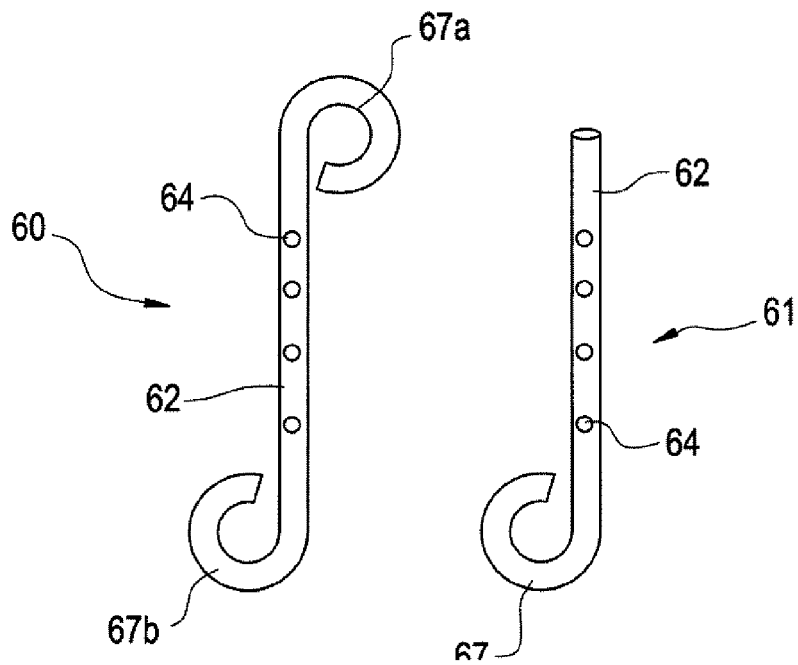
FIG. 6 is a plan view showing various embodiments of a drug delivery device having a retrieval coil on one or both ends of the device.

FIG. 6 shows linear body devices with retrieval coils provided on one or both ends of the elongated drug delivery devices. Devices 60 and 61 include a body which comprises a linear tube 62. An array of apertures are disposed in the tube and closed off by degradable timing membranes 64. Retrieval coils 67, 67a, 67b extend from ends of the tube 62.

The device may have a pigtail or a coiled part at one end or both ends. This coiled part can be used to promote the floatation of the device in the bladder with air entrapped as well as to facilitate the retrieval of the device. Each release orifice either shares a common drug reservoir or utilizes each partitioned reservoir. A coiled part can be made of elastic materials such as medical grade silicone or polyurethane. So, a pigtail part is spread during cystoscopic insertion of the device and returned to its original shape after the deployment. The connection between straight tube section and pigtail part(s) can be done by medical grade silicone adhesive. The release orifices covered with biodegradable timing membranes are not located at the coiled part to avoid the rupture of the membranes.

The size of the present implant devices can be made sufficiently small that irritation of the bladder trigone, which is responsible for creating the sensation of urgency of urination, is avoided or minimized. Consequently, the buoyant characteristic of the implant device is not expected to be critical. Nevertheless, irritation of the trigone region may also be minimized by selection of low density materials of construction or by entrapment of air or other gas in the device, although some of the volume for drug loading is sacrificed Another way to minimize irritation of the trigone region is to use low density materials.

II. Method of Making the Device

In one aspect, a method is provided for fabricating an implantable drug delivery device, which includes providing at least one tube having an outer surface, an inner surface, and at least one reservoir defined within the inner surface of the tube, wherein the tube is formed of a biocompatible material, which may be elastomeric, water permeable, or both elastomeric and water permeable; loading the reservoir in the tube with a drug formulation; forming one or more apertures through the sidewall of the tube; and forming a degradable membrane disposed over or in each of the one or more apertures to control the time of release of the drug formulation from the reservoir through the one or more apertures, wherein the tube can be elastically deformed to permit intravesical insertion of the drug delivery device.

The device body, the tube may be formed using conventional forming methods, such as injection molding, compression molding, extrusion molding, thermoforming, casting, or a combination thereof.

The step of forming one or more apertures may include laser drilling one or more holes in the side wall of the tube, using techniques known in the art. The laser drilling one or more holes may occur before or after the step of loading at the reservoir in the tube with the drug formulation. Alternatively, the apertures may be formed simultaneously with the device body, e.g., by molding with an indenter, as described in U.S. Pat. No. 6,808,522 to Richards et al.

The drug formulation can be stored in the reservoir in a solid form or a liquid form. If in liquid form, the drug formulation may be loaded into the reservoirs through the apertures or through another opening that it subsequently sealed. If in solid or semi-solid form, the drug formulation may be loaded, preferably in a solid form, into the reservoirs through an end opening in the tube, which opening subsequently is sealed.

In one embodiment, the drug formulation is loaded in the form of a solid or semi-solid rod. The solid form of drug is better than solution form because of its high drug concentration for a given volume, and also to facilitate handling of the device. High drug loading is important considering the importance of the small size of the device to minimize the irritation which might be caused by the implanted device.

To facilitate construction and handling of the device, it may be useful to prepare a solid or semi-solid rod of the drug formulation. This may be done with a relatively pure drug material, such as a polysaccharide or heparin sodium salt, or may require combination with another excipient or drug material to increase the stiffness of the drug formulation. For instance, lidocaine hydrochloride alone does not produce such a drug rod, but may be combined, e.g., in a 70:30 mixing ratio, with chondroitin sulfate C to produce a drug rod with some stiffness to enhance handling of the device. This mixing ratio significantly, however, sacrifices some of the payload of lidocaine hydrochloride. Whether that sacrifice is acceptable depends on the particular device design and application/use.

Figure 15:
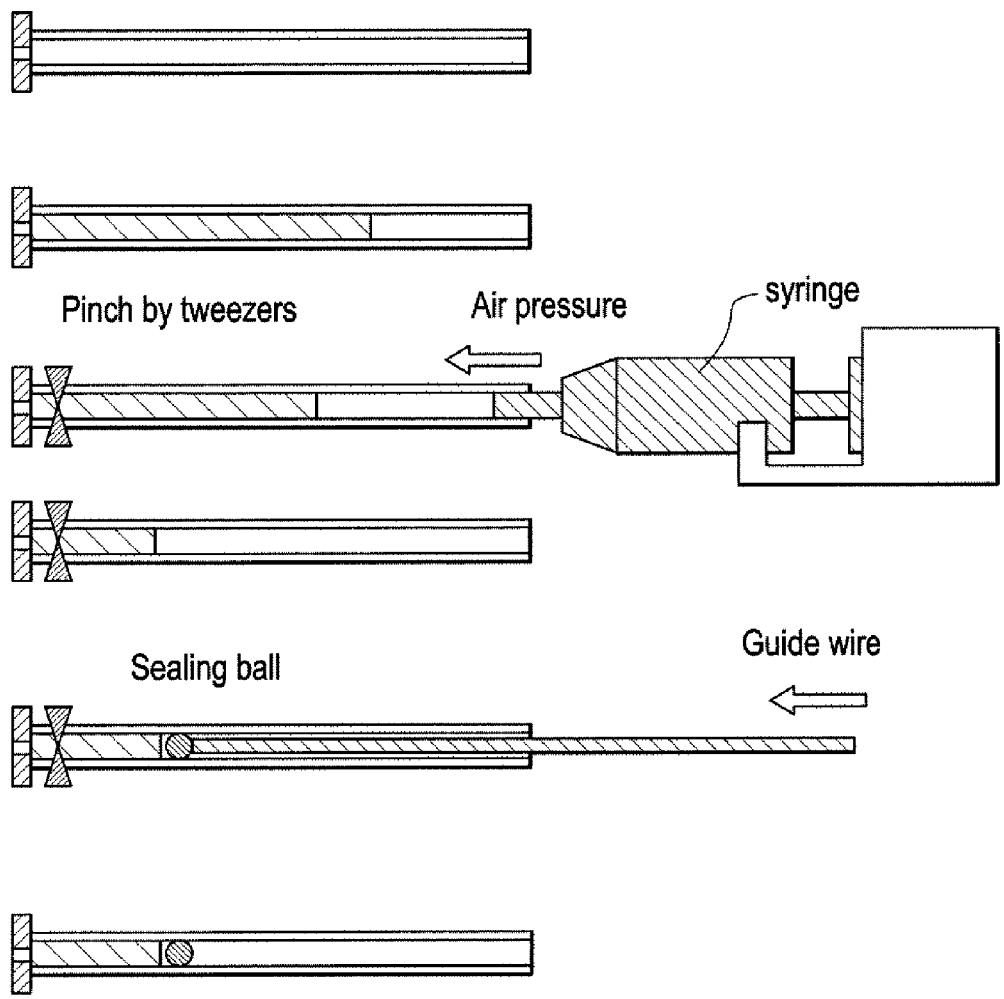
FIG. 15 shows, in cross-sectional views, the process steps in one embodiment of a method for assembling the device of FIG. 14.

One method of drug loading is illustrated in FIG. 15. The figure shows that the drug loading method implemented with the device with precision orifice, but this method can be also applied to the device with an laser drilled aperture in the sidewall of the tube of the device body. FIG. 15 shows, in order top to bottom, (i) an empty linear tube having a precision orifice disposed in one end with the other open, (ii) the central bore (reservoir) of the tube loaded with an aqueous drug solution; (iii) the tubing near the orifice pinched (e.g., by micro tweezers) to block off the orifice, and then air pressure applied from the other end while water is evaporated—permeated through the silicone tubing; (iv) yielding in the reservoir a drug formulation in a concentrated drug gel or solid cast rod form; (v) guide rod used to insert a sealing structure (e.g., microbead) through the tube opening to a position adjacent the drug formulation. In this way, one may control the position of the filling of the drug.

Silicone in different shapes can be used to form various forms of the solid drug. A flat silicone surface (or other material that wets the solution) can form a thin film of the drug when the drug solution is spread over it and allowed to dry. Tighter control of the thickness and surface uniformity can be achieved by creating a space of known dimensions between two blocks of silicone. This space can have almost any shape (such as a thin film or cylinder), as silicone can itself be shaped as needed to serve as a mold, Using silicone may have the advantage that water will diffuse out through it, but not the drug material of interest (e.g., polysaccharides), therefore making this process similar to a general casting process. Common casting shapes design guidelines apply to this process as well, such as channels for replenishing the solution inside the mold, in order to completely fill out the shape. Higher concentrations of the polysaccharide in solution may reduce the need for replenishing. Very high concentrations of polysaccharides may render the solution viscous, whereby the shaping process could proceed very similarly to a polymer extrusion process, but with minor allowances for the evaporation of water from the solution. Other solvents may also be used instead of water, as long as they do not denature the polysaccharides or other drug of interest. Silicone is not the only material that can be used as a mold. Almost any material can be used, as long as it does not dissolve in contact with the solution, forming potentially toxic compounds, and as long as there is a pathway for the solvent to evaporate from the solution.

The reservoir partition in a tube body can be installed simply by inserting the partition into the desired position within the tube, for example using a guide wire. This may be done alternating with the loading of the drug formulation, where multiple reservoirs and partitions are used. Its position can be secured by frictional engagement where the partition has a slightly larger outer diameter than the inner diameter of the tube. Alternatively or additionally, an adhesive may be used to fasten the partition in place.

The degradable membranes can be formed using a variety of techniques. In one embodiment, the degradable membranes are formed by microinjecting or inkjet printing a fluid to form a membrane at one end of the aperture, e.g., in/on the outer surface opening in the tube. For example, the fluid may be a solution comprising a resorbable material dissolved in a solvent, a suspension comprising a resorbable material in a nonsolvent, or a liquefied resorbable material.

FIG. 8 illustrates one embodiment of the manufacturing process, showing the various steps and possible variations in the order of the steps.

III. Use and Applications of the Device

The intravesical drug delivery device can be used to deliver drug locally to essentially any body cavity site. In a preferred embodiment, the body cavity is the bladder of a male or female human patient in need of treatment. For example, the intravesical drug delivery device can be used in the treatment of interstitial cystitis, overactive bladder syndrome, or bladder cancer. The device also could be used in the treatment of other conditions where drug needs to be delivered to the bladder and side effects with systemic delivery are unbearable or bioavailability is not high enough.

In other embodiments, the present intravesical devices may be used in other body cavities of a patient. For example, the small devices could be implanted in a space in the vagina, a gastric cavity, the peritoneal cavity, or an ocular cavity.

In one embodiment, a method for administering a drug to a patient is provided, which includes the steps of (1) implanting an intravesical drug delivery device into a body cavity of a patient wherein the intravesical drug delivery device comprises a body including at least one tube having an outer surface, an inner surface, and at least one reservoir defined within the inner surface of the at least one tube, wherein the at least one tube is formed of an elastomeric material so that the tube can be elastically deformed to permit intravesical insertion of the drug delivery device, a drug formulation contained in the at least one reservoir, one or more apertures through the sidewall of the at least one tube, a degradable membrane disposed over or in each of the one or more apertures to control the time of release of the drug formulation, and (2) releasing the drug formulation from the intravesical drug delivery device into the body cavity. In one example, the implantation is performed by passing the intravesical drug delivery device, in a linear form (e.g., folded or compressed form), through a catheter inserted into the urethra and the device is released within the bladder. U.S. Pat. No. 6,139,535 describes a method and apparatus for placement of a medical device in the bladder through the urethra.

In one embodiment, the intravesical drug delivery device is non-resorbable or otherwise needs to be removed following implantation. In one such a case, the method described in the preceding paragraph further includes step (3) removing the intravesical drug delivery device from the body cavity following release of the drug. Specialized retrieval devices are known in the art, or can readily be produced, for this purpose. U.S. Pat. No. 5,499,997 describes an endoscopic grasping method and apparatus.

In preferred embodiments, the device is administered to (i.e., implanted into) the bladder of a patient and delivers in a controlled manner a drug formulation to the bladder. In particular, the drug formulation includes one or more drugs useful in the treatment of overactive bladder syndrome, bladder cancer, interstitial cystitis, or pain relief.

The present intravesical drug delivery device treatment method provides extended, continuous, intermittent, or periodic release of a desired quantity of drug over a desired (predetermined) period of time. In one embodiment, the device can deliver the desired dose of drug over an extended period of time, e.g., 24 hours, 5 days, 7 days, 10 days, 14 days, or 20, 25, 30, 45, 60, or 90 days, or more. The rate of delivery and dosage of the drug can be selected depending upon the drug being delivered and the disease/condition being treated. The use of different degradation rates and/or excipient materials, along with varying the number and size of apertures in the device, can be used to tailor the device to have different release kinetics.

The implant devices may be secured within the body cavity, if necessary in certain embodiments, using techniques known in the art. For example, the device could be sutured (e.g., through a ring or other part of the device) or using a non-irritating adhesive, which may or may not be biodegradable.

The present invention may be further understood with reference to the following non-limiting examples.

Example 1

Casting of a Solid Drug Rod

Figure 9:
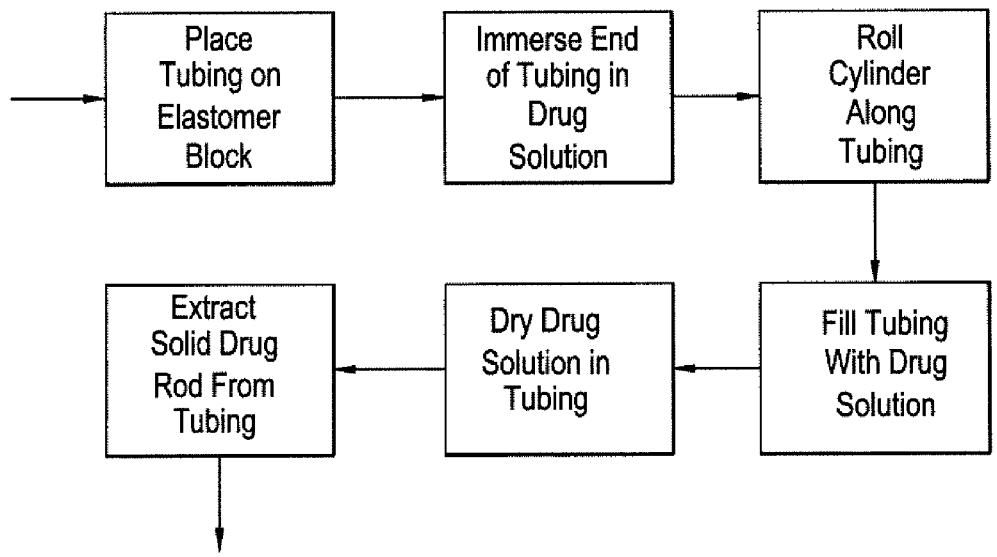
FIG. 9 is a process flow diagram illustrating a method for making a solid drug rod.
Figure 10:
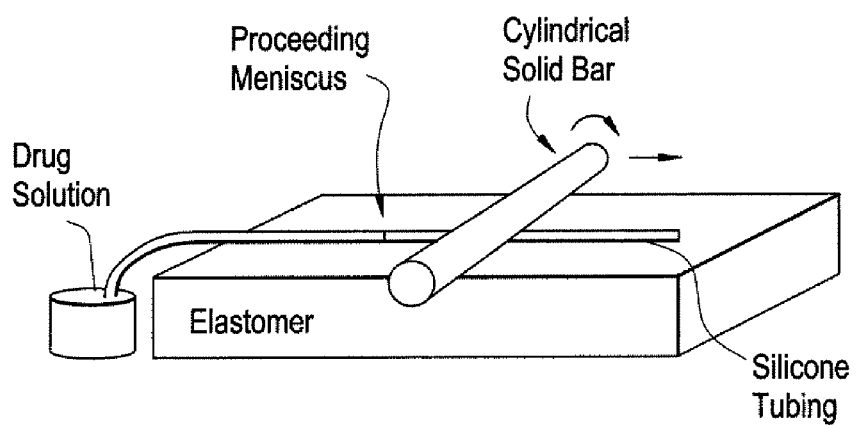
FIG. 10 is a schematic illustrating an embodiment of an apparatus for making solid drug rods.

A solid rod of drug formulation was made for use in loading an intravesical drug delivery vehicle. The process steps used in making the rod are illustrated in FIG. 9. Silicone tubing was placed on an elastomer block and one end of the tubing was immersed in a vial containing an aqueous solution of 25 weight % Chondroitin Sulfate C (CS—C). A cylinder bar was rolled along the length of the silicone tubing to induce peristaltic motion of the tubing, thereby filling the tubing with the concentrated drug solution. See FIG. 10. The drug solution in the tubing was allowed to dry overnight at room temperature until all water was evaporated, leaving a cast solid rod. The solid rod was extracted from the tubing using tweezers and was approximately 17% by volume of the original solution.

Example 2

Release of Polysaccharide from Device with 300 Micron Aperture

Figure 11:
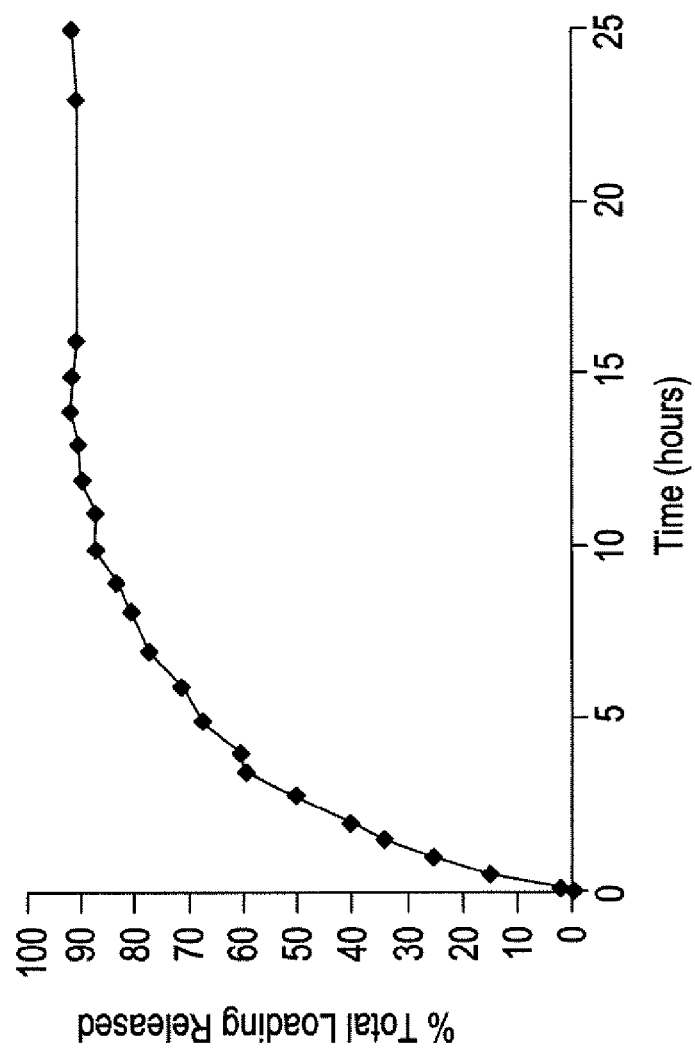
FIG. 11 is a graph showing percentage of total drug load released over time in vitro from one embodiment of the intravesical device in one experimental example releasing chondroitin sulfate C with a 300 μm aperture.

An implantable drug delivery device was prepared using silicone tubing having an inner diameter of 305 µm, outer diameter of 635 µm, wall thickness of 165 µm, and a length of 0.3 cm. A release orifice was drilled into the silicone tubing using laser ablation to produce an opening having a diameter of approximately 300 microns. A 316 µg solid rod of chondroitin sulfate C (CS—C), prepared as described in Example 1, was inserted into the silicone tubing and the tubing was plugged at both ends. The tubing was anchored and submerged in deionized water. Aliquots were collected and analyzed by a calorimetric assay using 1,9-dimethyl methylene blue (DMMB) to determine the concentration of CS—C released into the deionized water. FIG. 11 shows the percent of total drug released over 25 hours.

Example 3

Release of Polysaccharide from Device with 50 Micron Aperture

Figure 12:
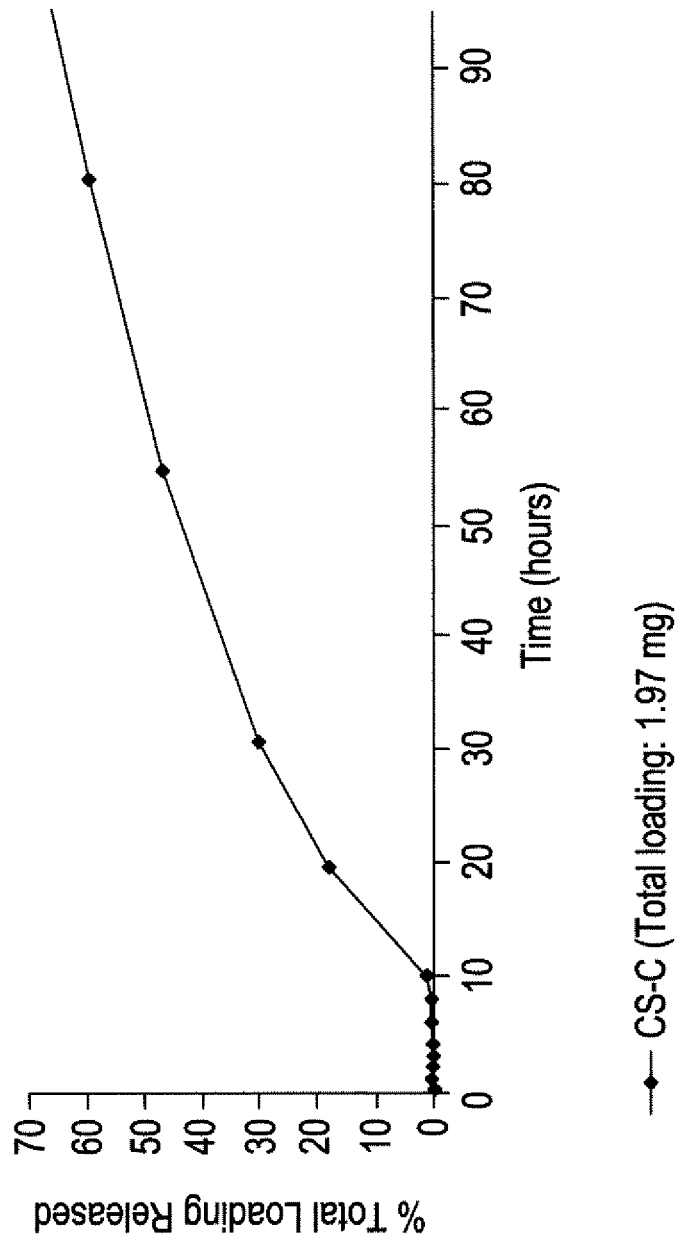
FIG. 12 is a graph showing percentage of total drug load released over time in vitro from one embodiment of the intravesical device in one experimental example releasing chondroitin sulfate C with a 50 μm aperture.

The test described in Example 2 was repeated using a device having a 2 cm length, a 50 micron aperture, and a total drug load of 1.97 mg of CS—C. FIG. 12 shows the percent of total drug released over 90 hours.

Example 4

Release of Polysaccharide and Lidocaine from Devices with 20 Micron Aperture

Figure 13:
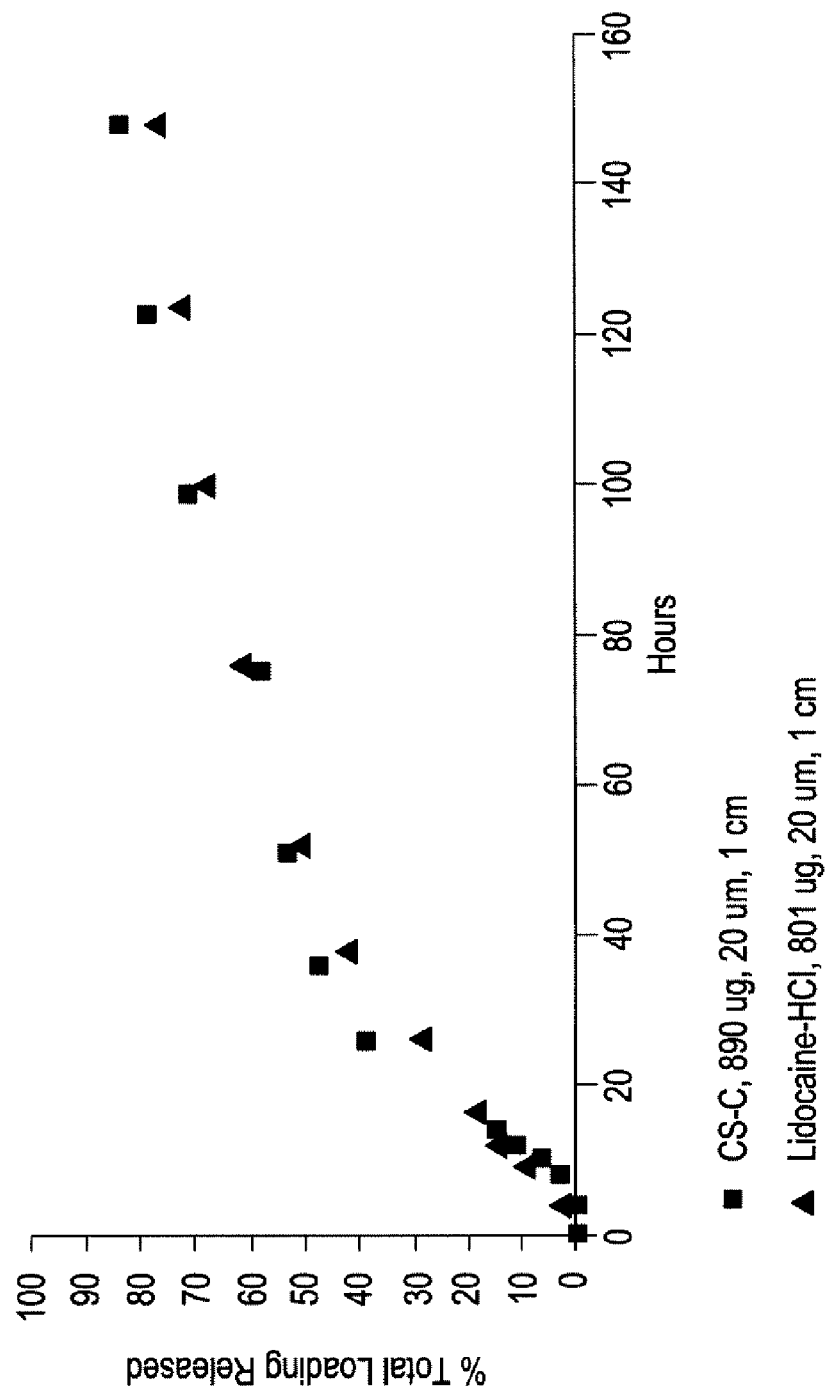
FIG. 13 is a graph showing percentage of total drug load released over time in vitro from one embodiment of the intravesical device in one experimental example releasing chondroitin sulfate C and lidocaine hydrochloride with a 20 μm aperture.

The test described in Example 2 was repeated twice using devices having a 1 cm length and a 20 micron precision orifice installed in an end of the tube (rather than a laser drilled orifice in the sidewall) each for a total drug load of 890 µg of CS—C and 801 µg of lidocaine hydrochloride. FIG. 13 shows the percent of total drug released over 160 hours, providing release profiles of both chondroitin sulfate C and lidocaine hydrochloride.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A drug delivery device for deployment into the urinary bladder of a patient, the drug delivery device comprising:
   a tubular body having an internal reservoir, the internal reservoir being in the form of an elongated central lumen with closed ends, the body comprising a wall which is at least partially non-resorbable; and
   a solid or semi-solid drug formulation housed within the internal reservoir of the body, the solid or semi-solid drug formulation comprising a drug,
   wherein the drug delivery device is deformable from a first configuration suited for passing the drug delivery device through a lumen of a urethral catheter or cystoscope into the bladder to a second configuration suited for retaining the device in the bladder,
   wherein the drug delivery device is configured to assume the second configuration upon exiting the urethral catheter or cystoscope, without an additional procedure to load a pharmaceutical solution into the device after the device is released into the bladder.

2. The device of claim 1, wherein the body is formed of a flexible material that permits elastically deforming the body between the first configuration and the second configuration.

3. The device of claim 1, wherein the wall defines the boundary of the internal reservoir and the solid drug formulation fills the internal reservoir.

4. The device of claim 3, wherein the wall is tubular in shape, the wall having an exterior surface and an interior surface, the interior surface defining the boundary of the reservoir, the drug formulation positioned directly adjacent to the interior surface.

5. The device of claim 4, wherein an aperture extends from the exterior surface to the interior surface to permit the drug to exit the reservoir once solubilized.

6. The device of claim 5, wherein the wall is configured to control the passage of water into the reservoir to solubilize the drug formulation at a suitable rate for release of the drug from the release aperture.

7. The device of claim 1, wherein the drug comprises lidocaine hydrochloride, glycosaminoglycans, pentosan polysulfate, dimethyl sulfoxide, chondroitin sulfate C, oxybutynin, mitomycin C, or a combination thereof.

8. The device of claim 1, wherein the device in its second configuration comprises a coil.

9. The device of claim 1, wherein the solid drug formulation is solid and substantially free of excipients.

10. The device of claim 1, wherein the body comprises silicone.

11. The device of claim 1, wherein the body is positioned about the solid drug formulation, the wall being elastomeric and at least in part controlling in vivo solubilization and release of the drug from the device.

12. The device of claim 11, wherein the elastomeric wall comprises silicone.

13. The device of claim 12, wherein the second configuration comprises a coil.

14. The device of claim 13, wherein the drug comprises lidocaine hydrochloride or another anesthetic agent.

15. The device of claim 1, wherein the tubular body has an overall shape which is curved when the device is in the second configuration.

16. A drug delivery device for deployment into the urinary bladder of a human patient, the device comprising:
   a water-permeable, silicone tubular body having an internal reservoir, the internal reservoir being in the form of an elongated central lumen with closed ends; and
   a solid drug formulation housed within the internal reservoir of the body, the solid drug formulation comprising lidocaine hydrochloride,
   wherein the drug delivery device is deformable from a first configuration suited for passing the drug delivery device through a lumen of a urethral catheter or cystoscope into the bladder to a second configuration suited for retaining the device in the bladder upon exiting the urethral catheter or cystoscope, the drug delivery device being configured to assume the second configuration upon exiting the urethral catheter or cystoscope without an additional procedure to load a pharmaceutical solution into the device after the device is released into the bladder,
   wherein the tubular body has at least one aperture therethrough and is configured to control release of the lidocaine hydrochloride through the aperture.

17. The device of claim 16, wherein the tubular body has an overall shape which is curved when the device is in the second configuration.

18. The device of claim 16, wherein the drug delivery device is constructed to exhibit buoyancy within the bladder.

19. The device of claim 16, wherein the at least one aperture has a diameter from 20 microns to 300 microns.

20. The device of claim 6, wherein the at least one aperture is configured to control release of the drug through the aperture at least in part by osmotic pressure.

21. A drug delivery device for deployment into the urinary bladder of a patient, the drug delivery device comprising:
   a body having an annular, tube-shaped, water permeable wall bounding a central lumen, the wall comprising silicone; and
   a solid drug formulation comprising a drug, the solid drug formulation being loaded in the central lumen,
   wherein the drug delivery device is deformable from a first configuration suited for passing the drug delivery device through a lumen of a urethral catheter or cystoscope into the bladder to a second configuration suited for retaining the device in the bladder upon exiting the urethral catheter or cystoscope,
   wherein the wall is configured to permit diffusion of water through the wall into the central lumen to solubilize the drug formulation and the body comprises at least one aperture configured to control release of the solubilized drug through the aperture at least in part by osmotic pressure.

22. The device of claim 21, wherein the at least one aperture has a diameter from 20 microns to 300 microns.

23. The device of claim 21, wherein the solid drug formulation fills the central lumen.

24. The device of claim 21, wherein the drug comprises lidocaine hydrochloride.

25. A drug delivery device for deployment into the urinary bladder of a patient, the drug delivery device comprising:
   a body having an annular, tube-shaped, water permeable wall bounding a central lumen, the lumen being elongated along a longitudinal axis and having a cross-section perpendicular to the longitudinal axis; and
   a solid drug formulation comprising a drug, the solid drug formulation disposed in the lumen and filling the cross-section of the central lumen,
   wherein the drug delivery device is deformable from an initial, uncompressed shape that is effective to prevent voiding of the device from the bladder to an elongated shape that is effective to permit deploying the device from a deployment instrument positioned in a urethra of the patient,
   wherein the drug delivery device is configured, upon exiting the deployment instrument, to return from the elongated shape to the initial shape, and
   wherein the wall is configured to permit diffusion of water through the wall into the central lumen to solubilize the drug formulation and the body comprises at least one aperture suited to dispense the solubilized drug driven at least in part by osmotic pressure in the central lumen.

26. The device of claim 25, wherein the drug comprises lidocaine hydrochloride.

27. The device of claim 25, wherein the at least one aperture has a diameter from 20 microns to 300 microns.

28. The device of claim 1, wherein at least one of the closed ends comprises an aperture to permit release of the drug from the reservoir following solubilization of the drug formulation.

29. The device of claim 16, wherein at least one of the closed ends comprises an aperture to permit release of the drug from the reservoir following solubilization of the drug formulation.

* * * * *

UNITED STATES PATENT AND TRADEMARK OFFICE
CERTIFICATE OF CORRECTION

PATENT NO. : 8,801,694 B2
APPLICATION NO. : 11/463956
DATED : August 12, 2014
INVENTOR(S) : Heejin Lee et al.

Page 1 of 1

It is certified that error appears in the above-identified patent and that said Letters Patent is hereby corrected as shown below:

In the Claims

Column 18, line 56, claim 9, after "the" delete "solid".

Signed and Sealed this
Second Day of December, 2014

Michelle K. Lee
*Deputy Director of the United States Patent and Trademark Office*